(12) United States Patent
Frigoli et al.

(10) Patent No.: US 6,281,366 B1
(45) Date of Patent: Aug. 28, 2001

(54) PHOTOCHROMIC [3H]NAPHTHO[2,1-B] PYRAN COMPOUNDS CONTAINING AN ACETYLENIC SUBSTITUENT, PROCESS FOR THEIR MANUFACTURE, AND PHOTOCHROMIC MATERIALS AND ARTICLES OBTAINED

(75) Inventors: Michel Frigoli; Corinne Moustrou; André Samat; Robert Guglielmetti, all of Marseilles (FR)

(73) Assignee: Essilor International Compagnie Generale d'Optique, Charenton Cedex (FR)

( * ) Notice: Subject to any disclaimer, the term of this patent is extended or adjusted under 35 U.S.C. 154(b) by 0 days.

(21) Appl. No.: 09/515,142

(22) Filed: Feb. 29, 2000

(51) Int. Cl.$^7$ ............ C07D 409/06; C07D 409/14; C07D 311/92
(52) U.S. Cl. ............ 549/59; 549/214; 549/389; 524/109; 524/110
(58) Field of Search ............ 549/389, 59, 214; 524/109, 110

(56) References Cited

U.S. PATENT DOCUMENTS 6,096,246 * 8/2000 Chan et al. ............ 252/586

OTHER PUBLICATIONS

Chem. Abstracts, 125;221395; Mughaddam et al, J. Chem. Res., Synopsis (1996), (7), p. 338–339.*
U.S. Patent application 09/349,686, filed Jul. 8, 1999.

* cited by examiner

Primary Examiner—Bernard Dentz
(74) Attorney, Agent, or Firm—Fulbright & Jaworski L.L

(57) ABSTRACT

The present invention relates to photochromic [3H]naphtho [2,1-b]pyran compounds containing an acetylenic substituent, process for their manufacture, and photochromic materials and articles obtained therefrom. The invention, in some specific aspects, relates to photochromic compounds having a [3H]naphtho-[2,1-b]pyran structure and bearing an acetylenic group in one of the positions 7 to 10 of the naphthopyran ring structure.

15 Claims, No Drawings

PHOTOCHROMIC [3H]NAPHTHO[2,1-B] PYRAN COMPOUNDS CONTAINING AN ACETYLENIC SUBSTITUENT, PROCESS FOR THEIR MANUFACTURE, AND PHOTOCHROMIC MATERIALS AND ARTICLES OBTAINED

FIELD OF THE INVENTION

The invention relates to photochromic compounds, more particularly heterocyclic compounds of the [3H]naphtho[2, 1-b]pyran family substituted with an acetylenic group, and to their application in the field of materials and articles with variable optical transmission.

BACKGROUND OF THE INVENTION

When photochromic compounds are subjected to irradiation containing ultraviolet rays (sunlight, xenon lamps or mercury lamps), they undergo a reversible color change. As soon as the excitation stops, they regain their original color.

In recent years, organic materials intended for optical applications have been the subject of considerable research. Ophthalmic glasses, glass for the construction industry, motor vehicle or airplane windshields and helmet visors, whose transparency in the visible range can be modified by using photochromic compounds, have particularly attracted attention. For this type of application using sunlight (heliochromism), the photochromic active compound must satisfy a certain number of criteria, among which are:

- high colorability in the visible range after excitation with light (colorability is a measure of the capacity of a photochromic compound to exhibit an intense color);
- an absence of coloration (or a weak coloration) in the initial state;
- rapid kinetics of thermal decolozization at room temperature;
- a high speed of coloration.

One of the major difficulties encountered with photochromic compounds is that of obtaining a compromise between high colorability and rapid decolorization kinetics. The reason for this is that, under continuous solar irradiation, a photostationary equilibrium is established between the molecules which become colored under the action of ultraviolet light and those which become decolorized under the conjugate action of temperature and visible light. Thus, frequently, an increase in the rate of decolorization entails a decrease in the colorability.

U.S. patent application Ser. No. 09/349,686 to Michel Frigoli et al, filed on Jul. 8, 1999 discloses a novel family of naphtho[2,1-b]pyrans substituted with bithienyl or terthienyl groups, which have particularly advantageous photochromic properties.

However, these novel naphtho[2,1-b]pyrans substituted with bithienyl or terthienyl groups, as well as the classical photochromic compounds of the naphtho[2,1-b]pyrans family, suffer of a lack of resistance to fatigue (also known as photodegradation of the photochromic compound).

In other words, the initial maximum colorability (Ao) of a photochromic compound decreases in time upon irradiation by visible light, and the resistance to fatigue of a photochromic compound is usually determined by measuring the time t for the colorability of the photochromic to decrease to a value equals to Ao/2 upon continuous irradiation by visible light. The longer is this time t the higher is the resistance to fatigue of the photochromic compound.

Thus, one object of the invention is to provide photochromic compounds having photochromic properties at least equivalent to those of the known photochromic compounds, in particular of the naphtho[2,1-b]pyrans family, but exhibiting significantly improved resistance to fatigue.

This combination of characteristics makes these novel compounds particularly advantageous for the manufacture of photochromic materials, in particular comprising a substrate made of transparent polymer material such as organic glasses with variable optical transmission (glass for sunglasses, glass for the construction industry, motor vehicle or airplane windshields, and riding or flying helmet visors).

The photochromic compounds can be incorporated directly into the organic glass substrate or dissolved in a polymer film stuck to the organic glass substrate.

SUMMARY OF THE INVENTION

The compounds which form the subject of the invention are [3H]naphtho[2,1-b]pyrans (I) bearing an acetylenic group on one of the positions 7 to 10, preferably position 8, of the naphto pyran ring structure.

DETAILED DESCRIPTION OF THE INVENTION AND PREFERRED EMBODIMENTS

A first class of the photochromic compounds according to the invention has formula:

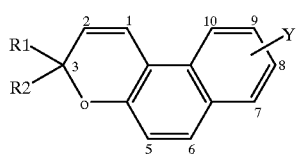

(I)

in which Y is an acetylenic group directly linked to one of the 7 to 10 positions of the naphthopyran ring structure and $R^1$ and $R^2$ are, independently from each other, H, alkyl, cycloalkyl, aryl or heteroaryl.

Preferably Y has formula:

in which R is H, alkyl, cycloalkyl, aryl or heteroaryl.

Preferably alkyl groups for R are $C_1$–$C_6$ alkyl groups, such as methyl, ethyl, propyl and butyl.

Preferred cycloalkyl groups are $C_5$–$C_7$ cycloalkyl groups such as cyclopentyl, cyclohexyl and cycloheptyl.

Preferred aryl groups for R are phenyl, substituted phenyl groups, naphtyl and substituted naphtyl groups.

Preferred heteroaryl groups for R are thienyl and bithienyl groups.

The most preferred aryl groups for R are the groups of formula:

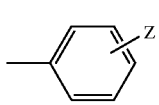 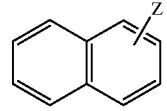

in which Z is H or an alkyl group, preferably a $C_1$–$C_6$ alkyl group such as methyl, ethyl.

Among the preferred heteroaryl groups are those of formulas:

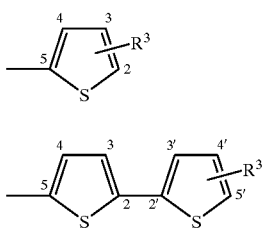

In which R³ denotes H or a substituent which can occupy one of the position 2, 3, 3', 4, 4' and 5'. Preferably, R³ as a substituent, occupies position 2 or 5'.

As a substituent, R³ is selected from the group consisting of alkyl groups, cycloalkyl groups, aryl groups, —OR', —SR', —COR' and —COOR' in which R' is H, an alkyl group, a cycloalkyl group, an aryl group, an amino group, —NO₂, —CN, —SCN, a halogen atom or a mono- or polyhaloalkyl group.

Preferred alkyl groups for R³ are $C_1$–$C_6$ alkyl groups, such as methyl, ethyl, propyl, butyl and hexyl, preferred cycloalkyl groups are $C_5$–$C_7$ cycloalkyl groups, such as cyclopentyl, cyclohexyl and cycloheptyl; preferred aryl groups are phenyl, a phenyl which is mono- or polysubstituted with one (or more) $C_1$–$C_6$ alkyl, $C_5$–$C_7$ cycloalkyl, phenyl and amino substituent(s); halogens preferably represent Br, Cl and F; and the mono- (or poly-) haloalkyl groups are preferably mono- (or poly)chloro or fluoro $C_1$–$C_6$ alkyl groups, for example —CF₃.

The most preferred heteroaryl groups are:

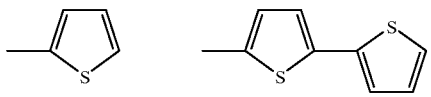

R¹ and R² which are identical or different, represent H, an alkyl group, preferably a $C_1$–$C_6$ alkyl group such as methyl, ethyl, propyl, a cycloalkyl group, preferably a $C_5$–$C_7$ cycloalkyl group, an aryl group, an heteroaryl group, a group —OR', —SR', —COR' and COOR', in which R' is as above.

Preferred aryl groups for R¹ and R² are those of formula:

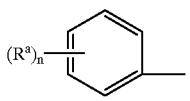

In which Rᵃ represents H, an alkyl group, an aryl group, a group —OR", —SR", —COR" and COOR", in which R" is defined as R' or is an amino group of formula NR⁴R⁵ in which R⁴ and R⁵ represent, independently from each other, an alkyl group, a cycloalkyl group, an aryl group, R⁴ and R⁵ being capable to form with the nitrogen carbon atom, an aromatic heterocycle having 4 to 7 links and optionally including one or more heteroatoms selected from oxygen, nitrogen and sulfur, and n is an integer from 1 to 5.

Preferred heteroaryl groups for R¹ and R² are Th 1 and Th 2 groups defined above.

The compound of formula (I) can be synthetized by Csp2-Csp Sonogashira-Hagihara coupling. This coupling is disclosed in Tetrahedron Letters, 50, 4467 (1975) K Sonogashira, Y Thoda and N Hagihara and in Synthesis, 571 (1984) A Carpita, A Leni, R. Roni.

This synthesis of the photochromic compounds of the invention may be represented as follows:

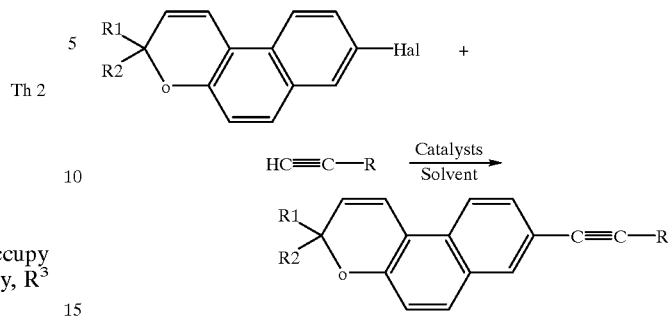

The following synthesis are given only as illustration of the use of the Sonogashira-Hagihara coupling reaction for preparing photochromic compounds according to the present invention.

Synthesis of 8-(3-hydroxy-3-methylbut-1-yn-1-yl)-3-3-diphenyl-[3H]-naphtho[2,1-b]pyran

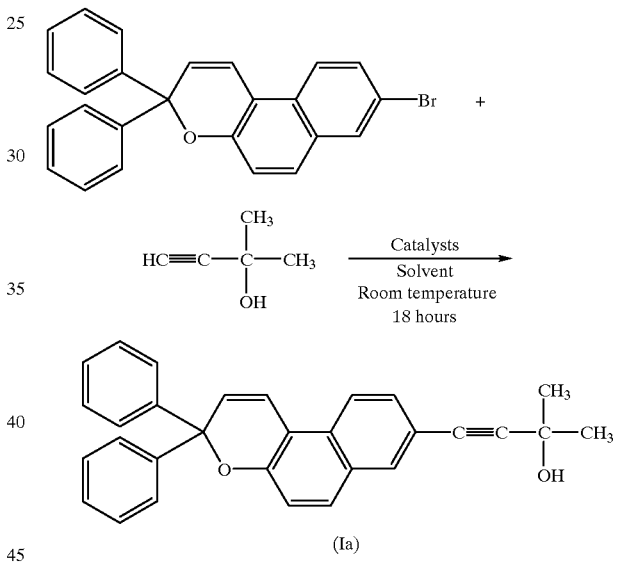

Catalysts: Copper (I) Iodide (Cu I)/bis[trisphenylphosphine]palladium (II) dichloride (Pd(PPh₃)₂Cl₂).

Solvent: (C₂H₅)₂NH.

Synthesis of preferred compounds of formulas

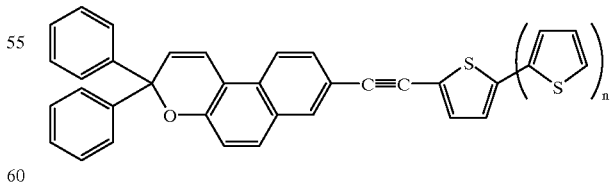

These compounds can be synthesized through the Sonogashira-Hagihara coupling reaction using the 8-(3-hydroxy-3-methylbut-1-yn-1-yl)-3,3diphenyl-[3H]-naphtho[2,1-b]pyran (Ia) above as an intermediate product.

The synthesis may be schematically represented as follows:

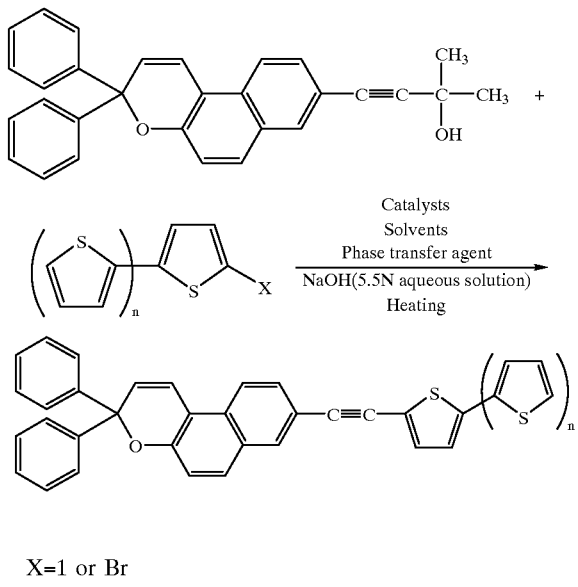

X=1 or Br n=0 or 1

Catalysts=Tetrakis[trisphenyl phosphine]palladium (Pd (PPh₃)₄) and Copper (I) iodide (CuI)

Solvent=Benzene

Phase transfer agent=Benzyl triethyl ammonium bromide $(C_6H_5CH_2N^+(C_2H_5)_3Br^-)$.

Synthesis of

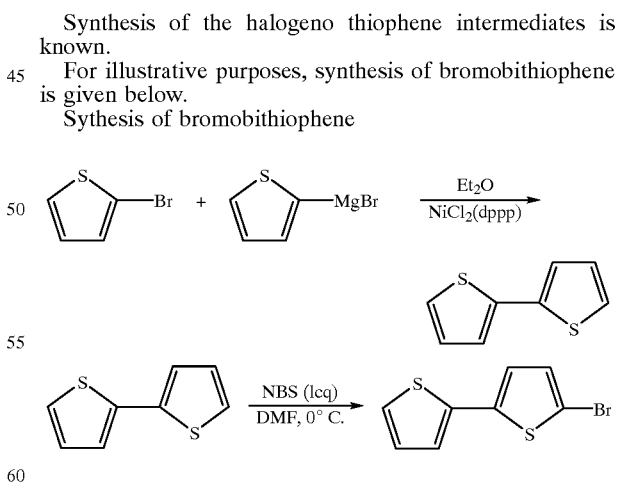

This photochromic compound may be synthesized using the Sonogashira-Hagihara coupling reaction according to the following scheme:

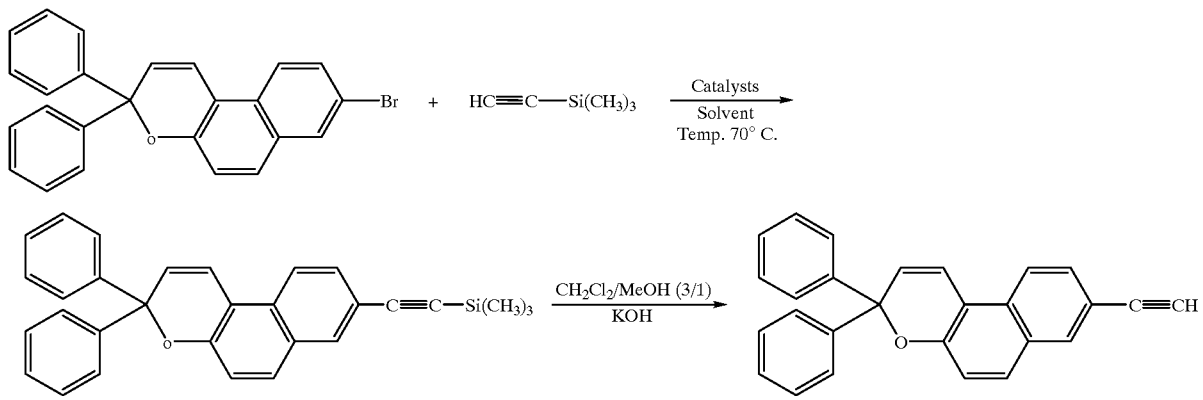

Synthesis of the halogeno thiophene intermediates is known.

For illustrative purposes, synthesis of bromobithiophene is given below.

Sythesis of bromobithiophene

NBS=N-Bromosuccinimide
DMF=Dimethyl formamide
Dppp=[1,3bis(diphenylphosphino)propane] dichloronickel(II)

A second class of preferred photochromic compounds according to the invention are bichromophoric compounds of the formula:

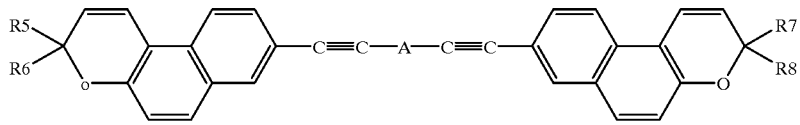

In which $R_5$, $R^6$, $R^7$ and $R^8$ identical or different represent the same groups as defined above for $R^1$ and $R^2$, and A is a divalent radical selected from:

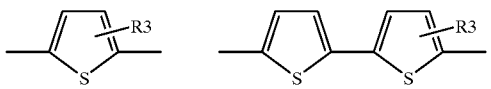

In which $R^3$ is defined as above and can occupy one of the positions 3, 3', 4, 4'.

These compounds of formula (II) may be synthesized in a similar manner as the compounds of formula (I) including a thiophenyl acetylenic substituent.

For example, the intermediate compound of formula (Ia) may be used to prepare bichromophoric compounds through the Songashira-Hagihara coupling reaction as follows:

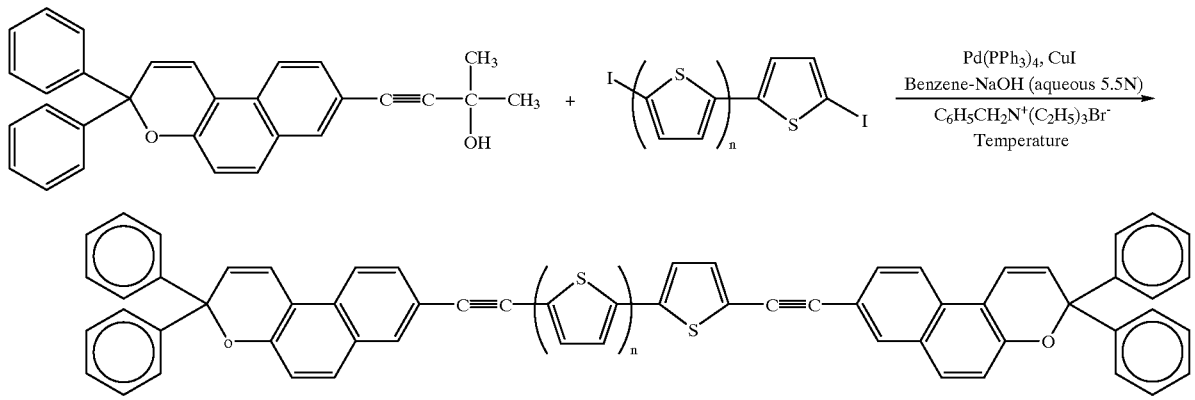

with n being 0 or 1.

The dihalogenated thiophene compounds may be prepared as previously indicated by using the requisite amounts of halogen.

For example, the di-iodo bithiophene compounds may be prepared according to the following reaction:

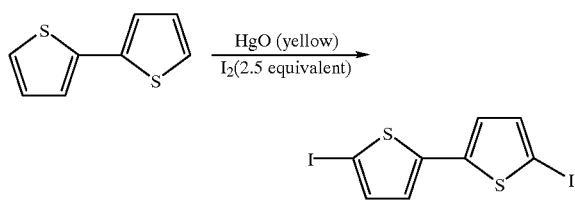

The naphthopyrans of the present invention show particularly advantageous photochromic properties when compared with those of molecules of the same family of the prior art. A main advantage of these novel compounds is that they exhibit improved fatigue resistance without impairing other valuable photochromic properties.

The compounds of the invention are particularly suitable for the preparation of transparent articles made of organic glass that absorbs ultraviolet rays of shorter wavelengths (glass for the construction industry and airplane or motor vehicle windshields), in particular for the manufacture of glass for spectacles or for riding or flying helmet visors.

The compounds in accordance with the invention can be introduced directly into a transparent polymer matrix or can be incorporated into a composition intended to be applied onto a transparent organic polymer material. In this case, the compounds which are the subject of the invention are dissolved in a suitable solvent (for example chloroform, ethyl acetate, acetone, acetonitrile, dichloromethane or benzene) and incorporated into a solution of polymer (for example polyurethane, polyacrylate, polymetharylate) in the same solvent.

The compositions are then applied in the form of a film a few micrometers thick on to a transparent polymer support (such as polycarbonate, cellulose acetate or polyalkyl acrylate), to obtain a photochromic material which can become colored in the presence of ultraviolet radiation and rapidly regains its non-colored and transparent state in the absence of a light source.

The compounds in accordance with the invention have the advantage of allowing this color change a large number of times at temperatures close to room temperature.

More specifically, the compounds in accordance with the invention may be introduced into a composition which is intended to be applied to or introduced into a transparent organic polymer material in order to obtain a transparent organic photochromic article. They may also be introduced into solid compositions such as plastic films, sheets and lenses in order to produce materials which may especially be used as ophthalmic lenses, sunglasses, visors, camera optical systems and filters, glass for the construction industry, airplane or motor vehicle windshields and helmet visors.

The liquid compositions which constitute one subject of the invention are essentially characterized in that they contain the compounds in accordance with the invention in dissolved or dispersed form in a solvent-based medium which are suitable for application to or introduction into a transparent polymer material.

Solvents which may more particularly be used are organic solvents chosen from benzene, toluene, choroform, dichloromethane, ethyl acetate, methyl ethyl ketone, acetone, ethyl alcohol, methyl alcohol, acetonitrile, tetrahydrofuran, dioxane, ethylene glycol methyl ether, dimethylformamide, dimethyl sulfoxide, methylcellosolve, morpholine and ethylene glycol.

When the compounds in accordance with the invention are dispersed, the medium may also contain water.

According to another embodiment, the compounds in accordance with the invention may be introduced into, and preferably dissolved in, colorless or transparent solutions prepared from transparent polymers, transparent copolymers or mixtures of transparent polymers in a suitable organic solvent.

Among the polymers and copolymers which may be mentioned are polyurethanes, poly(meth)acrylates, polyallyl (meth)acrylates, cellulose derivatives such as nitrocellulose, cellulose acetate and ethylcellulose, polyvinyl chloride, polystyrene, poly(alkyl)styrene and polyvinylpyrrolidone.

Examples of such solutions are, inter alia, solutions of nitrocellulose in acetonitrile, of polyvinyl acetate in acetone, of polyvinyl chloride in methyl ethyl ketone, of polymethyl methacrylate in acetone, of cellulose acetate in dimethylformamide, of polyvinylpyrrolidone in acetonitrile, of polystyrene in benzene, and of ethylcellulose in methylene chloride.

These compositions may be applied to transparent supports, such as supports made of polyethylene glycol terephthalate, of borylated paper, or of cellulose triacetate, and dried in order to obtain a photochromic material, which may become colored in the presence of ultraviolet radiation and which returns to the colorless and transparent state in the absence of the source of radiation.

The photochromic compounds of the present invention, or the compositions containing them, which are defined above may be applied to or incorporated into a solid transparent polymerized organic material which is suitable for transparent articles such as ophthalmic lenses, or into useful materials for use in sunglasses, visors, camera, optical systems and filters, glass for the construction industry, airplane or motor vehicle windshields and helmets visors.

By way of solid transparent materials which may be used to produce ophthalmic lenses in accordance with the invention, there may be mentioned polyol(allylcarbonate) polymers, polyacrylates, poly(alkyl acrylates) such as polymethyl methacrylates, cellulose acetate, cellulose triacetate, cellulose acetate propionate, cellulose acetate butyrate, poly (vinylacetate), poly(vinyl alcohol), polyurethanes, polycarbonates, polyethylene terephthalates, polystyrenes, poly(stryrenemethyl methacrylate)s, copolymers of styrene and acrylonitrile, and polyvinyl butyrates.

The transparent copolymers or mixtures of transparent polymers are also suitable for producing such materials.

There may be mentioned in this respect, materials prepared from polycarbonates, such as poly(4,4'-dioxy-2,2-diphenylpropane), polymethyl methacrylate, polyol(allyl carbonate)s, in particular such as diethylene glycol bis(allyl carbonate) and the copolymers thereof, for example such as with vinyl acetate. The copolymers of diethylene glycol bis(allyl carbonate) and of vinyl acetate (80–90/10–20) may be mentioned in particular, and also the copolymer of diethylene glycol bis(allyl carbonate) with vinyl acetate, cellulose acetate and cellulose propionate, and cellulose butyrate (80–85/15–20).

The polyol(allyl carbonates are prepared using allyl carbonates of linear or branched, aliphatic or aromatic liquid polyols, such as aliphatic bis(allyl carbonate) glycols or alkylene bis(allyl carbonate)s. Among the polyol(allyl carbonate)s that can be used to prepare the solid transparent materials which may be used in accordance with the invention, there may be mentioned ethylene glycol bis(allyl carbonate), diethyl glycol bis(2-methallyl carbonate), diethylene glycol bis(allyl carbonate), ethylene glycol bis-(2-chloroallyl carabonate), triethylene glycol bis(allyl carbonate), 1,3-propanediol bis(allyl carbonate), propylene glycol bis(2-ethylallyl carbonate), 1,3-butanediol bis(allyl carbonate), 1,4-butanediol bis(2-bromoallyl carbonate), trimethylene glycol bis(2-ethylallyl carbonate), pentamethylene glycol bis(allyl carbonate), and isopropylenebisphenol bis(allyl carbonate). The most important product consists of diethylene glycol bis(allyl carbonate), also known under the name CR39®.

The amount of photochromic compounds to be used in accordance with the invention, either in the composition or at the time of its introduction into the solid support, is not critical and generally depends on the intensity of the color that the composition may impart to the material after exposure to radiation. Generally speaking, the more photochromic compounds are added, the more intense will be the coloration under irradiation.

In accordance with the invention, an amount is used which is sufficient to impart to the treated material the property of changing color at the time of exposure to radiation. This amount of photochromic compounds is generally between 0.01 and 20% by weight, and preferably between 0.05 and 10% by weight, relative to the total weight of the optical material or of the composition.

The photochromic compounds in accordance with the invention may also be introduced into a temporary transfer support (such as a varnish which forms a coating on a substrate) and then be thermally transferred into the substrate, as described in particular in U.S. Pat. No. 4,286,957 or U.S. Pat. No. 4,880,667.

These compounds can be used with other photochromic compounds, such as photochromic compounds which give rise to different colorations such as blue or green and which are known in the prior art. Thus, spiro(indolino-oxazines), which are well-known in the prior art, can be used.

The following examples illustrate the present invention.

In the examples, unless otherwise stated, all parts and percentages are by weight.

Melting points (M.p.) were determined in capillary tubes on a Büchi-510 apparatus and are uncorrected.

Chemical structure of the compounds was confirmed by Fourier transform IR spectrum recorded on a Matson-Polaris spectrophotometer from samples as KBr pellets, and $^1$H and $^{13}$C NMR spectra recorded with Bruker AC 250 (250 MHz) or AMX 400 (400 MHz). $^1$H NMR spectra were referenced internally to the residual proton resonance in $CDCl_3$($\delta$7.24 ppm), or with tetramethylsilane (TMS, $\delta$0.00 ppm) as internal standard. $^{13}$C NMR were referenced to $CDCl_3$($\delta$77.0 for centerline).

Column chromatographies were performed on silica gel 60 (MERCK 7734). Triethylamine, diethylamine and benzene were purchased from Aldrich.

The reactions were conducted in oven-dried (120° C.) glassware under argon atmosphere. All solvents for palladium catalysed coupling reactions were degassed and saturated with argon before use.

The commercially available ($Pd(PPh_3)_2Cl_2$ and $Pd(PPh_3)_4$ (Aldrich, Strem respectively) were used as received.

The following compounds were prepared according to literature procedures: 5-bromo-2,2'-bithiophene[1][2], 5,5'- diodo-2,2'-bithiophene[3] and 5-iodo-2,2': 5',2"-terthiophene[4].

Preparation of 8-bromo-3,3-diphenyl-[3]-naphtho[2,1-b]pyran

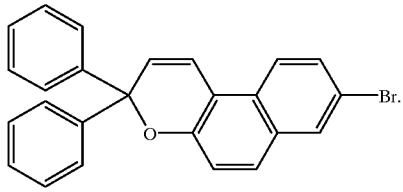
(1)

Under argon, a solution of 3 g (14.4 mmol) of 1,1-diphenyl-2-propyn-1-ol, 3.53 g (1.58 mmol) of 6-bromo-2-naphthol and paratoluene sulfonic acid (catalytic amount) in dry $CH_2Cl_2$ (30 ml) was stirred at room temperature for 3 days. The disappearance of the propargylic alcohol was monitored by thin-layer chromatography (eluent: pentane/$Et_2O$, 80/20). The mixture was concentrated under reduced pressure. The crude product was purified by chromatography on silica gel using pentane/$Et_2O$ (100:0 to 70:30) gradient to afford 4.76 g (80%) of compound (1) as a white solid.

M.p. 149.5° C.

Anal. calc. for $C_{25}H_{17}Obr$: C, 72.64; H, 4.14; Found: C, 72.60; H, 4.13.

EXAMPLE 1

Prepartion of 8-(3-hydroxy-3-methylbut-1-yn-1-yl)-3,3-diphenyl-[3H]-naphtho[2,1-b]pyran

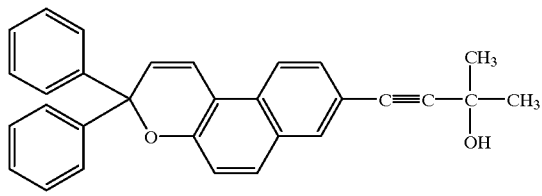
(Ia)

Bis[triphenylphosphine]palladium (II) dichloride (0.203 g, 0.29 mmol) and copper (I) iodide (30 mg, 0.145 mmol) were added successively to compound (I) (600 mg, 1.45 mmol) and 2-methylbut-3-yn-2-ol (366 mg, 4.35 mmol) in diethylamine (15 ml) under argon at room temperature.

After stirring for 16 hours at room temperature, diethylamine was removed in vacuo. The residue diluted with benzene (30 ml), was filtered through Celite®. Calite® was washed carefully with benzene. Benzene was removed under reduced pressure, and the residue was purified by silica gel column chromatography using pentane/acetone (100:0 to 50:50) gradient to give (Ia) (580 mg, 96%) as a pale yellow solid.

Recrystallization from pentane/$CH_2Cl_2$ gave crystalline material.

M.p. 75–76° C.

Anal. calc. for $C_{30}H_{24}O_2$: C, 86.50; H, 5.81; Found: C, 86.40; H, 5.76.

EXAMPLE 2

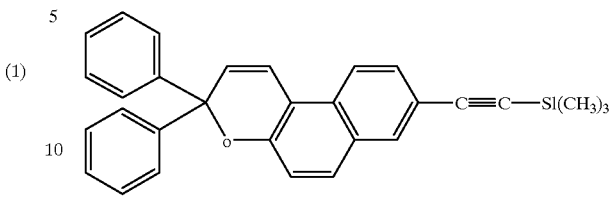
(Ib)

Preparation of 8-(trimethylsilylethynyl)-3,3-diphenyl-[3H]-naphtho[2,1-b]pyran

A mixture of compound (I) (1.5 g, 3.63 mmol), trimethylsilylacetylene (713 mg, 7.26 mmol), bis[triphenylphosphine)palladium dichloride (510 mg, 0.726 mmol), copper (I) iodide (69 mg, 0.363 mmol) and anhydrous triethylamine (20 ml) was stirred at 70° C. for 24 hours. The reaction mixture was allowed to cool to room temperature and triethylamine was removed under reduced pressure. The residue obtained, diluted into benzene (30 ml) was filtered through Celite®. Benzene was removed, the residue was purified by chromatography on silica gel using pentane/$Et_2O$ (100:0 to 80:20) gradient to yield 1.20 g (77%) of (Ib) as a white solid.

Recrystallization from hexane/$CH_2Cl_2$ gave crystalline material.

M.p. 177° C.

Anal. calc. for $C30H_{26}OSi$: C, 83.67; H 6.09; Found: C, 83.79; H, 6.11.

EXAMPLE 3

Preparation of 8(ethynyl)3,3-diphenyl-[3H]-naphtho[2,1-b]pyran

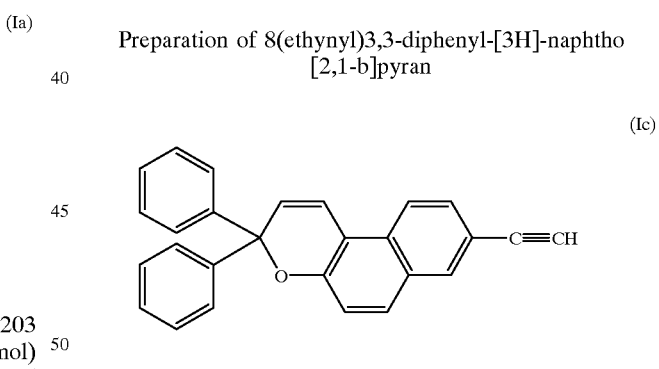
(Ic)

To a solution of (Ib) (839 mg, 1.95 mmol) in $CH_2Cl_2$ (15 ml), a solution of KOH (327 mg, 5.85 mmol) in MeOH (10 ml) was added dropwise. The reaction mixture was stirred for 3 hours at room temperature, The solvents were removed and the residue diluted with $Et_2O$ (30 ml).

After washing with water (2×20 ml), the organic layer was dried over $MgSO_4$. Concentration and chromatographic purification over silica gel furnish (Ic) (670 mg, 96%) as a white solid.

Small amount of (Ic) was recrystallized from hexane/$CH_2Cl_2$.

M.p. 143° C.

Anal. calc. for $C_{27}H_{18}O$: C, 90.47; H, 5.06; Found: C, 90.52; H, 5.10

EXAMPLES 4 TO 5 a) Characterization of thiophenic compounds:

5-bromo-2,2'-bithiophene

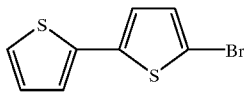

M.p. 33° C. [Lit.[1] 33–34° C.].

5,5'-diiodo-2,2'-bithiophene

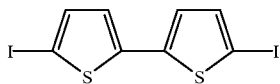

M.p. 164° C. [Lit.[3] 165–166° C.].

b) Thiophenic acetylenic derivatives: general procedure

To a deaerated solution of compound (Ia) (300 mg 0.721 mmol), the appropriate thiophenic halide (0.865 mmol) in benzene (15 ml), are successively added copper (I) iodide (6 mg, $3.24 \times 10^{-5}$ mol), tetrakis[triphenylphosphine] palladium (37 mg, $3.24 \times 10^{-5}$ mol) and benzyltriethylammonium chloride (5 mg, $2.3 \times 20^{-5}$ mol).

A deaerated 5.5 normal aqueous solution of sodium hydroxide (15 ml) is then added and the reaction mixture is stirred for 24–72 hours at 70° C. (The disappearance of the compound (Ia) was monitored by thin-layer chromatography (eluent: pentane/CH$_2$Cl$_2$, 80/20)).

After cooling to room temperature, the mixture was filtered through Celite®. Celite® was washed with benzene. The filtrate was decanted. The aqueous layer was extracted into benzene (2×10 ml). The combined organic phase was washed with water (3×20 ml), dried over MgSO$_4$, and filtered. After the solvent was removed, the residue was purified by silica gel column chromatography using pentane/CH$_2$Cl$_2$ (100/0 to 70/30) gradient to afford the thiophenic acetylenic derivative.

Recrystallization from hexane/CH$_2$Cl$_2$ gave crystalline material.

EXAMPLE 4

8-[2(thien-2-yl)ethynyl]-3,3-diphenyl-[3H]-naphtho[2,1-b]pyran (Id)

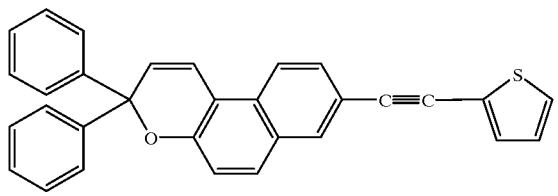

Light brown solid

Yield: 88%.

M.p.: 220.1° C.

Anal. calc. for C$_{31}$H$_{20}$OS: C, 84.51; H, 4.58; S, 7.27; Found: C, 84.32; H, 4.62; S, 7.20.

EXAMPLE 5

8-[2,2'-bithien-5-yl)ethynyl]-3,3-diphenyl-[3H]-naphtho[2,1-b]pyran (Ie)

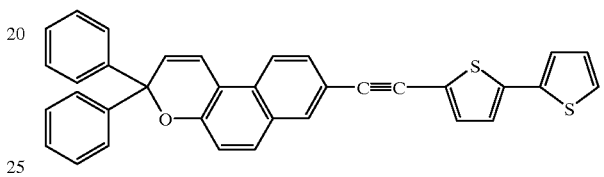

Yield: 60%

M.p. 185° C.

Anal. calc. for C$_{35}$H$_{22}$OS$_2$: C, 80.42; H, 4.24; S, 12.27; Found: C, 80.21; H, 4.36; S, 12.10

EXAMPLES 6 AND 7

Thiophenic biacetylenic derivatives: general procedure

To a deaerated solution of compound (Ia) (400 mg, 0.961 mmol), the appropriate thiophenic dihalide (0.457 mmol) in benzene (20 ml) are rapidly added copper (I) iodide (9 mg, $4.6 \times 10^{-5}$ mmol), tetrakis[triphenylphosphine]palladium (52 mg, $4.6 \times 10^{-5}$ mol) and benzyltriethylammonium chloride (11 mg, $4.6 \times 10^{-5}$ mol).

A deaerated 5.5 normal aqueous solution of sodium hydroxyde (20 ml) is then added and the reaction mixture is stirred for 48–72 hours at 70° C. (The disappearance of the compound (Ia) was monitored by thin-layer chromatography (eluent: pentane/CH$_2$Cl$_2$, 80/20)).

The biphasic mixture was allowed to cool and filtered through Celite®. Celite® was washed carefully with benzene, and the layers were separated. The aqueous layer was extracted with benzene (2×20 ml); and the combined organic layers were washed with water (3×25 ml), brine (3×25 ml), and finally dried (MgSO$_4$). The solvent was filtered and evaporated. The residue was purified by silica gel column chromatography using pentane/CH$_2$Cl$_2$ (100/0 to 50/50) gradient to give the thiophenic biacetylenic derivative.

Recrystallization from benzene gave crystalline material.

EXAMPLE 6

2,5-bis[(3,3diphenyl-[3H]-naphtho[2,1-b]pyran-8-yl)ethynyl]thiophene

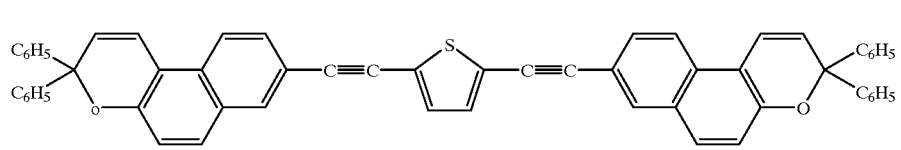

(IIa)

Yield: 73%

M.p. 137° C. (yellow solid)

Anal calc. for $C_{58}H_{36}O_2S$: C, 87.40; H, 4.55; S, 4.02; Found: C, 87.15; H, 4.70; S, 4.10.

EXAMPLE 7

5,5'-bis[(3,3-diphenyl-[3H]-naphtho[2,1-b]pyran-8-yl)ethynyl]-2,2'-bithiophene

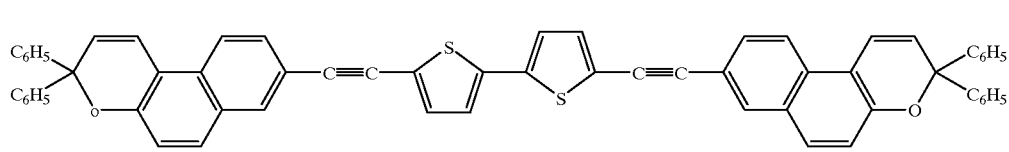

(IIb)

Yield: 80%

M.p. >270° C. (orange solid)

Anal. calc. for $C_{62}H_{38}O_2S_2$: C, 84.70; H, 4.36; S, 7.29; Found: C, 83.54; H, 4.15; S, 7.00.

[1] P. Bäuerle, F. Würthner, G. Götz, F. Effenberger, *Synthesis,* 1993, 1099

[2] D. A. Forsyth, D. E. Vogel, *J. Org. Chem.,* 1979, 22, 2917

[3] L. L. Miller, Y. Yu. *J. Org. Chem.,* 1995, 60, 6813

[4] A. Mac Eachern, C. Soucy, L. C. Leitch, J. T. Arnason, P. Morand, *Tetrahedron,* 1988, 9, 2403.

Evaluation of photochromic properties $2.5 \cdot 10^{-5}$ M solutions in toluene of compounds according to the invention and prior art photochromic compounds for comparison were prepared.

The maximum absorption wavelength of the colored form (λ max), the thermal bleaching rate constant (KΔ) and colorability (Ao) at λ max were determined using the above toluene solutions by irradiation with a Flash-photolysis apparatus (Nortech) coupled to a fast spectrometer Warner and Swasey. The conditions were as follows:

Cells length: 10 cm

Temperature: 25° C.

Flash energy: 60 J

The fatigue resistance was measured by irradiating continuously a sample of the above solutions with a xenon lamp of 250 W and measuring the time t at which the absorbance of the coloured form reaches the Ao/2 value.

The results are given in table 1.

| Compound | λ max (nm) | Ao | KΔ (s⁻¹) | t (Ao/2) (minutes) |
|---|---|---|---|---|
| Comparative compound A | 432 | 0.84 | 0.09 | 456 |
| Compound Ia | 456 | 1.10 | 0.18 | 1015 |

-continued
| Compound | λ max (nm) | Ao | KΔ (s⁻¹) | t (Ao/2) (minutes) |
|---|---|---|---|---|
| Compound Ib | 464 | 1.25 | 0.03 / 0.19 | 859 |
| Compound Ic | 448 | 1.20 | 0.032 / 0.19 | 1042 |
| Compound Id | 471 | 3.10 | 0.03 / 0.20 | 598 |
| Compound Ie | 484 | 5.30 | 0.07 / 0.23 | — |
| Compound IIa | 476 | 7.1 | 0.004 / 0.21 | 601 |
| Compound IIb | 480 | 1.4 | 0.05 / 0.19 | 1700–1800 estimated |
| 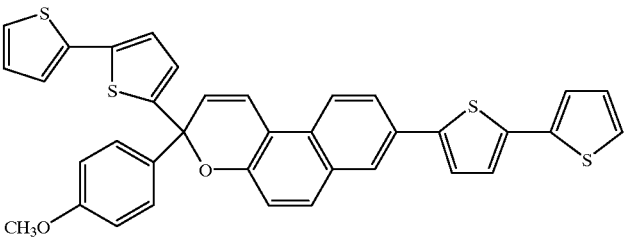 Comparative compound B | 549 | 8.00 | 0.55 / 0.18 | Average ≈250 |
| 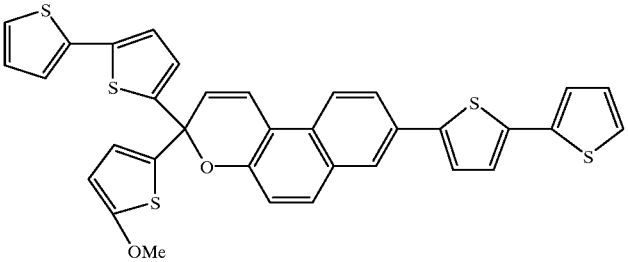 Comparative compound C | 560 | 7.80 | 1.22 / 0.30 | |
| 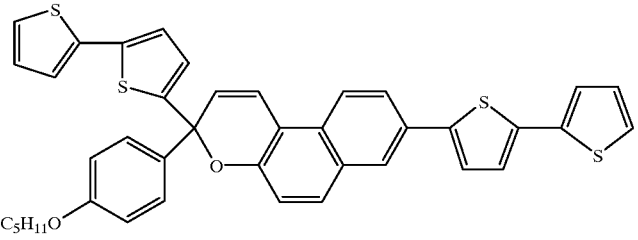 Comparative compound D | 548 | 8.00 | 0.48 / 0.18 | |
| 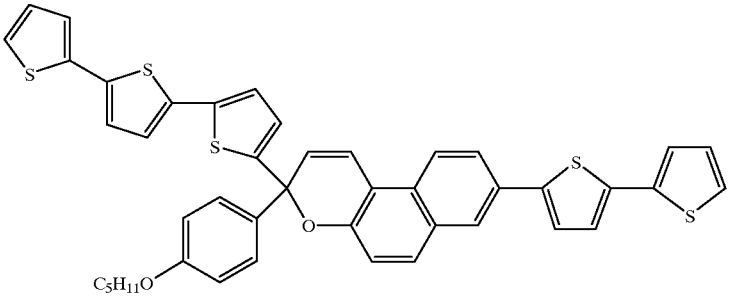 Comparative compound E | 564 | 11.00 | 0.47 / 0.16 | |

What is claimed is:

1. Photochromic compound having [3H]naphtho-[2,1-b] pyran structure and bearing an acetylenic group directly linked to one of the positions 7 to 10 of the naphthopyran ring structure through a carbon of the acetylenic group.

2. Photochromic compound according to claim 1, wherein the acetylenic group is in position 8.

3. Photochromic compound according to claim 1, corresponding to the formula:

(I)

in which Y is an acetylenic group directly linked to one of the positions 7 to 10 of the naphthopyran ring structure and R1 and R2 represent, independently from each other, a hydrogen atom, an alkyl group, a cycloalkyl group, an aryl group or a heteroaryl group.

4. Photochromic compound according to claim 3, wherein Y is in position 8.

5. Photochromic compound according to claim 1, wherein the acetylenic group has formula

—C≡C—R in which R represents H, an alkyl group, a cycloalkyl group, an aryl group or a heteroaryl group.

6. Photochromic compound according to claim 5, wherein R is an heteroaryl group of formula in which $R^3$ represents H or a substituent which can occupy one of the position 2, 3, 3', 4 and 5' and is selected from alkyl groups, cycloalkyl group, aryl groups, —OR', —SR', —COR', —COOR' where R' is H, an alkyl group, a cycloalkyl group, an aryl group, an amino group, —NO$_2$, —CN, —SCN, a halogen atom or a mono-or polyhaloalkyl group.

7. Photochromic compound according to claim 1, wherein $R^1$ and $R^2$ are selected from groups of formula:

in which $R^a$ represents H, an alkyl group, an aryl group, a group —OR", —SR,"—COR" and COOR", in which R" is defined as R' in claim 6 or is an amino group of formula NR$^4$R$^5$ in which $R^4$ and $R^5$ represent, independently from each other, an alkyl group, a cycloalkyl group, an aryl group, $R^4$ and $R^5$ being capable to form with the nitrogen atom, an aromatic heterocycle having 4 to 7 links and optionally including one or more heteroatoms selected from oxygen, nitrogen and sulfur, and n is an integer from 1 to 5.

8. Photochromic compound according to claim 7, wherein $R^1$ and $R^2$ represent a phenyl group.

9. Photochromic compound according to claim 1, having the formulas:

10. Photochromic compound according to claim 1, having formula:

in which $R^5$, $R^6$, $R^7$ and $R^8$ identical or different represent the same groups as defined for $R^1$ and $R^2$, and A is a divalent radical selected from:

in which $R^3$ is defined as in claim 6 and can occupy one of the positions 3, 3', 4, 4'.

11. Photochromic compound according to claim 10, wherein $R^5$, $R^6$, $R^7$ and $R^8$ are phenyl groups and $R^3$ is a hydrogen atom.

12. Transparent article comprising a substrate made of transparent polymer material, in which at least one photochromic compound according to claim 1 is incorporated into the substrate.

13. Transparent article comprising a substrate made of transparent polymer material, in which at least one face of the article is coated with a film made of transparent polymer material incorporating at least one photochromic compound according to claim 1.

14. Article according to claim 12, in which the article is glazing for the construction industry, a motor vehicle or airplane windshields, a helmet visor or a spectacle glass.

15. Article according to claim 13, in which the article is glazing for the construction industry, a motor vehicle or airplane windshield, a helmet visor or a spectacle glass.

* * * * *